United States Patent [19]
Forfang et al.

[11] Patent Number: 6,162,792
[45] Date of Patent: *Dec. 19, 2000

[54] USE OF SPIRAMYCIN FOR TREATING GASTROINTESTINAL DISORDERS CAUSED BY *H. PYLORI*

[75] Inventors: Erik T. Forfang, Jar; Sven-Erik Larssen, Oslo, both of Norway

[73] Assignee: Aventis Pharma S.A., Antony Cedex, France

[*] Notice: This patent issued on a continued prosecution application filed under 37 CFR 1.53(d), and is subject to the twenty year patent term provisions of 35 U.S.C. 154(a)(2).

[21] Appl. No.: 08/727,466
[22] PCT Filed: Apr. 24, 1995
[86] PCT No.: PCT/FR95/00533
  § 371 Date: Oct. 22, 1996
  § 102(e) Date: Oct. 22, 1996
[87] PCT Pub. No.: WO95/28943
  PCT Pub. Date: Nov. 2, 1995

[30] Foreign Application Priority Data

Apr. 25, 1994 [FR] France ................... 94 04952

[51] Int. Cl.[7] ................ A61K 31/70; A61K 31/415; A61K 33/24
[52] U.S. Cl. ................ 514/29; 514/30; 514/398; 424/653
[58] Field of Search ................ 514/24, 30, 398, 514/29; 424/653

[56] References Cited

FOREIGN PATENT DOCUMENTS

375068 A1  6/1990  European Pat. Off. .

OTHER PUBLICATIONS

Axon, V. *Helicobacter pylori* therapy: Effect on peptic ulcer disease, J. Gastroenterol. Hepatol., vol. 6, No. 2, pp. 131–137 (1991).

The Merck Index, 11th Ed., 1989, pp. 8703, 8720, 9130, 9131.

*Primary Examiner*—Jerome D. Goldberg
*Attorney, Agent, or Firm*—Irving Newman

[57] ABSTRACT

Gastrointestinal disorders involving *Helicobacter pylorid* are treated by administering spiramycin or spiramycin/metronidazole combinations. In addition, administration of anti-ulcer agents may be carried out before, during or after such administration of spiramycin or spiramycin/metronidazole combinations. Pharmaceutical compositions for such administrations are also disclosed.

26 Claims, No Drawings

USE OF SPIRAMYCIN FOR TREATING GASTROINTESTINAL DISORDERS CAUSED BY *H. PYLORI*

The present invention relates to a new therapeutic application of spiramycin optionally in combination with metronidazole.

Spiramycin, optionally in combination with metronidazole, may be useful for the preparation of a medicinal product intended for the prevention or treatment of gastrointestinal disorders involving *Helicobacter pylori*.

Numerous cases of peptic ulcers are identified each year. These ulcers are usually treated with anti-ulcer agents such as anti-$H_2$, bismuth derivatives or proton pump inhibitors. However, these are long-term treatments which are very expensive, which are not easily accepted by patients and in which numerous relapses are observed.

*Helicobacter pylori*, which was isolated for the first time from the gastric mucous membrane in 1982, is responsible for gastropathies such as gastritis and peptic ulcers, and is probably also responsible for the appearance of gastric cancers. The eradication of *Helicobacter pylori* greatly modifies the extent of ulcer diseases. Not only do the ulcers disappear rapidly (about 90%), but cases of relapses are almost completely eliminated.

Treatments for eradicating *Helicobacter pilori* by means of compositions comprising an antibacterial agent and an anti-ulcer agent are already mentioned in patent applications EP 206 625, EP 282 131 and WO 92/04 898 and WO 93/21 920.

However, numerous publications report manifestations of intolerance which appear in 20 to more than 40% of patients, in most cases consisting of nausea and diarrhea, but also of abdominal pain. These side effects result from the nature of the products currently used in clinical medicine, the high doses which have to be administered and the duration of the treatments.

Furthermore, the majority of effective therapies consist in the administration of 3 medicinal products, which is poorly accepted by patients. Thus, the practitioner is confronted with the difficult choice between the potency of the treatment, the limitation of the side effects and the poor acceptance by the patient for such a medication.

Spiramycin is a well known antibacterial agent isolated from *Streptomyces ambofaciens*: U.S. Pat. No. 2,943,023, U.S. Pat. No. 2,978,380 and U.S. Pat. No. 3,011,947.

Metronidazole is a nitroimidazole derivative which is also known (U.S. Pat. No. 2,944,061) and which is endowed with a parasiticidal and antibacterial action. The spiramycin/metronidazole combination marketed under the name Rodogyl® is known for its action on anaerobic microbes of the dentibuccal flora.

However, the activity of spiramycin or of its combinations with metronidazole does not suggest that an action can be observed in clinical medicine on a microbe which is difficult to eradicate, such as *Helicobacter pylori* for which it is usually necessary to use much more potent antibacterial agents, with the consequences that are known.

It has now been shown that it is possible to obtain the eradication of *Helicobacter pylori* by the administration of spiramycin or of a spiramycin/metronidazole combination, with a level of side effects which is completely reduced compared with other treatments.

The administration is carried out before, after or at the same time as the administration of an anti-ulcer agent.

The anti-ulcer agents are chosen equally well from the antacids, the anti-$H_2$ agents and the proton pump inhibitors.

The antacids may be especially bismuth derivatives or combinations of aluminium hydroxide and magnesium hydroxide such as Maalox®.

The anti-$H_2$ agents may be for example ranitidine, cimetidine, famotidine and the like.

The proton pump inhibitors may be for example omeprazole, lansoprazole, partoprazole and the like.

Among the spiramycin/metronidazole combinations, more particularly preferred is the combination which comprises Rodogyl® (750,000 I.U. spiramycin base/125 mg metronidazole combination). This pre-existing combination makes it possible, moreover, to administer only one antibacterial proprietary medicinal product during the treatment.

The activity was demonstrated in a 10-day treatment in patients suffering from peptic ulcers.

25 patients suffering from peptic ulcers were included according to the following criteria:

inclusion: motivated 18 to 80 year old men and women suffering from a benign duodenal or gastric ulcer confirmed by high endoscopy and having undergone a positive urease test using tissue collected by biopsy, prior to the treatment [G. Nysaeter, K. Berstad and al., Tidsskr Nor Laegeforen, 112, 2397–9 (1992)];

exclusion: patients who may exhibit risks of allergy to one of the medicinal products administered, pregnant women or women not on contraceptives, patients having other gastrointestinal diseases which may modify the interpretation of the test, as well as patients receiving another anti-ulcer agent at the time of inclusion in the study or having relapsed after prior treatment for eradicating *Helicobacter pylori*.

TREATMENT

Spiramycin (Rovamycine®) 1,500,000 I.U. and 150 mg of bismuth subnitrate in the form of a 1.5% solution (10 ml) are administered every 2, 4 times per day (or in total 6 million I.U. of spiramycin and 600 mg of bismuth subnitrate. 400 mg of metronidazole (Flagyl®) are administered 3 times per day. The same treatment is followed for 10 days, the spiramycin and metronidazole are administered during meals and the bismuth between meals. During the following weeks, the patients receive no other anti-ulcer medication.

A questionnaire relating to the side effects were submitted to each patient. The questionnaire is identical to that submitted during previous studies of eradication of *Helicobacter pylori* [K. Berstad et al., Is there a place for antacids in treatment of *Helicobacter pylori* infection?, Scand. J. Gastroenterol., 27, 1006–1010 (1992)]. The side effects have been classified as "slight" (do not limit the usual daily activities), moderate, (limit the daily activities to some extent) and "severe" (make the daily activities impossible).

Eradication of *Helicobacter pylori* and cure of the ulcers:

A respiration test and another endoscopy are carried out 4 weeks after stopping the treatment. In the case where an ulcer might be detected, the treatment would be considered a failure and the patient would receive a conventional treatment. Urease tests using tissue collected by biopsy, and a respiration test using $^{14}C$-urea [K. Bergstad et al., Biometric evaluation of gastric urease activity in man, Scand. J. Gastroenterol., 27, 977–83 (1992)] are carried out.

RESULTS 2 patients, one who refused to submit to the treatment up to the end, the other to submit to the tests, are excluded from the study. The results below relate to the other 23 patients.

7 women and 16 men with an average age of 53.9 years (ranging from 31 to 81 years) were included, in whom the disease had lasted on average for 18.7 years, namely for 1 to 40 years according to the cases. 19 of them had already previously had a peptic ulcer confirmed by endoscopy. 5 had already had a previous operation for their ulcers and 5 had previously been hospitalized for peptic ulcer accompanied by bleeding.

At the time of inclusion, 10 patients had a declared duodenal ulcer, 7 had a gastric ulcer and 1 had a pyloric ulcer. 5 patients suffered from duodenitis or gastritis, but with cured ulcers. These last 5 patients had undergone an intermediate treatment with an anti-$H_2$ agent. All the patients had dispeptic symptoms and a urease test using tissue collected by biopsy which was positive.

Healing of the ulcers:

4 weeks after the treatment, 21 of the 23 patients no longer had ulcers. The healing rate is 91.3% (confidence interval 72.0 to 98.9%).

Eradication of *Helicobacter Pylori:*

20 patients obtained a negative $^{14}$C-urea based respiration test, indicating the eradication of *Helicobacter pylori*, that is to say an eradication rate of 87.0% (confidence interval 66.4 to 97.2%). A perfect agreement was observed between the urease test and the respiration test, with the exception of only one patient.

Side effects:

Among the patients who took the treatment up to the end, 4 suffered from nausea, 16 from diarrhea and 4 from abdominal pain. Nevertheless, as a whole, the side effects were classified as "slight", that is to say not disrupting the usual daily activities, with the exception of only 2 patients for whom the effects were considered to be "severe".

It was thus possible to obtain rates of eradication of *Helicobacter pyrlori* and of healing of the ulcers similar to the rates for the best treatments, but with a treatment of shorter duration than some known treatments and in particular side effects which were widely reduced since only 2 patients out of 24 experienced side effects hampering their usual daily activity. (In similar studies, upon administration of other antibacterial agents, moderate to severe diarrhea was observed in 41.5% of the patients, which is considerably higher than 1 out of 23, or 4.4% in the present study).

The present invention also relates to the pharmaceutical compositions comprising spiramycin, optionally combined with metronidazole, intended for the prevention or treatment of gastrointestinal disorders involving *Helicobacter pylori*.

As compositions for oral administration, there may be used tablets, gelatin capsules, pills, powders freeze-dried products or granules. These compositions may contain the active ingredient(s) in the pure state or optionally in combination with one or more diluents, lubricants or adjuvants which are compatible and pharmaceutically acceptable.

By way of example, the compositions may contain excipients such as starch, dextrin, gelatine, polyvinylpyrrolidone, hydrated alumina, hydrated silica, dicalcium phosphate, magnesium stearate, sorbitol, mannitol, lactose, sucrose, citric acid and the like.

It is of course understood that the doctor will adapt the dosage to the subject to be treated. More particularly, the daily dosage may be between 0.75 and 10 million I.U. of spiramycin optionally combined with 125 to 1,500 mg of metronidazole in 2 to 3 doses.

The compositions according to the invention will be used in all cases of prevention or treatment of gastrointestinal disorders involving Helicobacter pylori, especially gastric ulcers, duodenal ulcers, oesophageal ulcers, gastritis, pre-pyloric ulcers, nonulcerous dyspepsia, gastric cancers.

What is claimed is:

1. A pharmaceutical composition comprising a combination of spiramycin and an anti-ulcer agent, said combination being effective to treat or prevent gastrointestinal disorders involving *Helicobacter pylori*, said effect of said combination being greater than the additive effect of separate treatment with one or the other of said spiramycin and said anti-ulcer agent.

2. The pharmaceutical composition according to claim 1, wherein the anti-ulcer agent is selected from the group consisting of antacids, anti-$H_2$ agents and proton pump inhibitors.

3. The pharmaceutical composition according to claim 2, wherein the anti-ulcer agent is an antacid.

4. The pharmaceutical composition according to claim 3, wherein the antacid is a bismuth derivative.

5. The pharmaceutical composition according to claim 4 wherein the bismuth derivative is bismuth subnitrate.

6. The pharmaceutical composition according to claim 2 wherein the anti-ulcer agent is selected from bismuth derivatives, combinations of aluminum hydroxide and magnesium hydroxide, ranitidine, cimetidine, famotidine, omeprazole, lansoprazole and pantoprazole.

7. A method for treating or preventing gastrointestinal disorders involving *Helicobacter pylori* comprising administering to a patient afflicted with or subject to said disorder an effective amount of metronidazole and an effective amount of spiramycin, said effect of said combination being greater than the additive effect of separate treatment with one or the other of said spiramycin and said metronidazole.

8. The method according to claim 7, further comprising administering to said patient an effective amount of an anti-ulcer agent.

9. The method according to claim 8, wherein the anti-ulcer agent is administered before, during or after administering the spiramycin and the metronidazole.

10. The method according to claim 7 further comprising administering to said patient an effective amount of an anti-ulcer agent selected from bismuth derivatives, combinations of aluminum hydroxide and magnesium hydroxide, ranitidine, cimetidine, famotidine, omeprazole, lansoprazole and pantoprazole.

11. A method for treating or preventing gastrointestinal disorders involving *Helicobacter pylori* comprising administering to a patient afflicted with or subject to said disorder an effective amount of spiramycin and an effective amount of an anti-ulcer agent, said effect of said combination being greater than the additive effect of separate treatment with one or the other of said spiramycin and said anti-ulcer agent.

12. The method according to claim 11, wherein the anti-ulcer agent is administered before, during or after administering the spiramycin.

13. The method according to claim 11 wherein the anti-ulcer agent is an antacid.

14. The method according to claim 13 wherein the antacid is a bismuth derivative.

15. The method according to claim 14 wherein the bismuth derivative is bismuth subnitrate.

16. The method according to claim 11 wherein said anti-ulcer agent is selected from bismuth derivatives, combinations of aluminum hydroxide and magnesium hydroxide, ranitidine, cimetidine, famotidine, omeprazole, lansoprazole and pantoprazole.

17. A pharmaceutical composition comprising a combination of spiramycin and metronidazole, said combination being effective to treat or prevent gastrointesting disorders involving *Helicobacter pylori,* said effect of said combination being greater than the additive effect of separate treatment with one or the other of said spiramycin and said metronidazole.

18. The pharmaceutical composition according to claim 17, further comprising an effective amount of an anti-ulcer agent.

19. The pharmaceutical composition according to claim 18, wherein the anti-ulcer agent is selected from the group consisting of antacids, anti-$H_2$ agents and proton pump inhibitors.

20. The pharmaceutical composition according to claim 17 further comprising an anti-ulcer agent selected from bismuth derivatives, combinations of aluminum hydroxide and magnesium hydroxide, ranitidine, cimetidine, famotidine, omeprazole, lansoprazole and pantoprazole.

21. The pharmaceutical composition according to claim 18 wherein the anti-ulcer agent is an antacid.

22. The pharmaceutical composition according to claim 21 wherein the antacid is a bismuth derivative.

23. The pharmaceutical composition according to claim 22 wherein the bismuth derivative is bismuth subnitrate.

24. The method according to claim 8 wherein the anti-ulcer agent is an antacid.

25. The method according to claim 24 wherein the antacid is a bismuth derivative.

26. The method according to claim 25 wherein the bismuth derivative is bismuth subnitrate.

* * * * *